United States Patent
Dursun et al.

(10) Patent No.: US 10,487,651 B2
(45) Date of Patent: Nov. 26, 2019

(54) REAL-TIME MONITORING OF HEALTH HAZARDS DURING HYDRAULIC FRACTURING

(71) Applicant: LANDMARK GRAPHICS CORPORATION, Houston, TX (US)

(72) Inventors: Serkan Dursun, Missouri City, TX (US); Ilyas Uyanik, Houston, TX (US); Olivier R. Germain, Houston, TX (US)

(73) Assignee: Landmark Graphics Corporation, Houston, TX (US)

( * ) Notice: Subject to any disclaimer, the term of this patent is extended or adjusted under 35 U.S.C. 154(b) by 126 days.

(21) Appl. No.: 15/039,348

(22) PCT Filed: Dec. 26, 2013

(86) PCT No.: PCT/US2013/077825
§ 371 (c)(1),
(2) Date: May 25, 2016

(87) PCT Pub. No.: WO2015/099736
PCT Pub. Date: Jul. 2, 2015

(65) Prior Publication Data
US 2017/0022807 A1 Jan. 26, 2017

(51) Int. Cl.
*E21B 49/08* (2006.01)
*E21B 43/26* (2006.01)
(Continued)

(52) U.S. Cl.
CPC .......... *E21B 49/08* (2013.01); *E21B 41/0021* (2013.01); *E21B 43/26* (2013.01);
(Continued)

(58) Field of Classification Search
None
See application file for complete search history.

(56) References Cited

U.S. PATENT DOCUMENTS

| 2005/0012035 A1 | 1/2005 | Miller |
| 2006/0173580 A1 | 8/2006 | Desrochers et al. |

(Continued)

FOREIGN PATENT DOCUMENTS

EP 2378058 A2 10/2011

OTHER PUBLICATIONS

Dutta et al., "Demo Abstract: Common Sense: Participatory Urban Sensing Using a Network of Handheld Air Quality Monitors" SenSys'09, Nov. 4-6, 2009.*

(Continued)

*Primary Examiner* — John C Kuan
(74) *Attorney, Agent, or Firm* — Locke Lord LLP (57) ABSTRACT

A real-time silica monitoring system can include a plurality of off-site sensors positioned at geographic locations off-site from a hydraulic fracturing well site that detect and measure quantities of airborne silica particles, a plurality of on-site sensors positioned at geographic locations on a hydraulic fracturing well site that detect and measure quantities of air-borne silica particles, and one or more mobile sensors suitable to be carried by individual persons that detect and measure quantities of airborne silica particles. A monitoring system can include a computer system that can aggregate and store airborne silica measurements taken by one or more sensors and communicate data to a user.

12 Claims, 4 Drawing Sheets

(51) Int. Cl.
    G06Q 50/22      (2018.01)
    E21B 43/267     (2006.01)
    E21B 41/00      (2006.01)
    G01N 33/00      (2006.01)
    G01N 15/06      (2006.01)
    G01N 15/00      (2006.01)
    G01N 1/22       (2006.01)
    G01N 1/02       (2006.01)

(52) U.S. Cl.
    CPC .......... *E21B 43/267* (2013.01); *G06Q 50/22* (2013.01); *G01N 1/2273* (2013.01); *G01N 15/06* (2013.01); *G01N 33/0075* (2013.01); *G01N 2001/021* (2013.01); *G01N 2015/0042* (2013.01)

(56) References Cited

U.S. PATENT DOCUMENTS

| | | | |
|---|---|---|---|
| 2008/0210430 | A1 | 9/2008 | Al-Muraikhi |
| 2009/0081804 | A1 | 3/2009 | Tuchman |
| 2009/0113990 | A1* | 5/2009 | Groves ............... G01N 1/2273 73/31.01 |
| 2012/0014749 | A1 | 1/2012 | Bonroy |
| 2013/0110402 | A1 | 5/2013 | Godager |
| 2013/0174646 | A1 | 5/2013 | Godager |

OTHER PUBLICATIONS

Young, Lee, PCT Search Report for PCT Application No. PCT/US13/77825 dated Apr. 17, 2014.
Young, Lee, PCT Written Opinion for PCT Application No. PCT/US13/77825 dated Apr. 17, 2014.
James Coe, Ohio State University, "One Room—63 Different Dust Particles? Researchers Aim to Build Dust Library", downloaded at http://researchnews.osu.edu/archive/dustlib.htm on Aug. 7, 2013.
MCVS, Head PM2,5 High Volume Sampler PM1025/UNE downloaded at http://www.mcvsa.com/Productes/Atm%C3%B3sfera/CabezaIPM25CaptadorAltoVolumenPM1025UNE/tabid/143/Default.aspx on Aug. 7, 2013.
Osha Quick Card, Silicosis downloaded at https://www.osha.gov/Publications/silicosis.html on Aug. 7, 2013.
Katie Weatherford, "New Study Shows Workers at Fracking Sites Exposed to Unsafe Levels of Silica Dust", Center for Effective Government, Aug. 5, 2013 downloaded from http://www.foreffectivegov.org/blog/new-study-shows-workers-fracking-sites-exposed-unsafe-levels-silica-dust.
Report on Silica Sand Environmental Quality Board, Minnesota Environmental Quality Board, dated Mar. 20, 2013 downloaded from http://www.eqb.state.mn.us/documents/23.%20March%20Final%20Silica%20Sand%20report.pdf.
Esswein, "Worker Exposure to Crystalline Silica During Hydraulic Fracturing", Center for Disease Control and Prevention, dated May 23, 2012 downloaded from http://blogs.cdc.gov/niosh-science-blog/2012/05/23/silica-fracking/.
Coal Mining & Rock Drilling downloaded from http://www.silicosis-injury-attorneys.com/pages/rockdrillers_risks.html on Aug. 7, 2013.
Dave Fehling, "Like Working in a Refinery: Fracking's New Chemical Hazards for Workers", downloaded at http://stateimpact.npr.org/texas/2012/07/24/like-working-in-a-refinery-frackings-new-chemical-hazards-for-workers/on Jul. 24, 2012.
Center for Disease Control, "SILICA", downloaded at http://www.cdc.gov/niosh/topics/silica/ on Aug. 7, 2013.
Center for Disease Control, "Preventing Silicosis and Deaths in Rock Drillers", DHHS (NIOSH) Publication No. 92-107, Aug. 1992, downloaded from http://www.cdc.gov/niosh/docs/92-107/.
Examiners Letter for Canadian Application No. 2931597 dated Apr. 3, 2017.
International Preliminary Report on Patentability for PCT Application No. PCT/US2013/077825 dated Jun. 28, 2016.
Examiners Letter for Canadian Application No. 2931597 dated Apr. 7, 2018.
Esswein et al., "Occupational Exposures to Respirable Crystalline Silica During Hydraulic Fracturing", Journal of Occupational and Environmental Hygiene, vol. 10, Issue 7, pp. 347-356, 2013.

* cited by examiner

REAL-TIME MONITORING OF HEALTH HAZARDS DURING HYDRAULIC FRACTURING

FIELD OF INVENTION

The embodiments disclosed herein relate generally to methods and systems for monitoring levels of airborne hazardous materials with stationary and mobile sensors and desktop and mobile applications; and more particularly relate to monitoring levels of airborne crystalline silica dust.

BACKGROUND OF INVENTION

Hydraulic Fracturing is becoming an increasingly important technique for producing oil and natural gas from portions of hydrocarbon formations which may have been previously inaccessible. Hydraulic Fracturing is a process of injecting oil and gas wells with water, sand and specialized chemicals at very high pressure. This process can involve hundreds of thousands of pounds of fracturing sand or "frac sand," which may result in airborne silica dust. Although there are many benefits to using Hydraulic Fracturing techniques to produce natural gas and oil resources, there are also concerns about possible Health-Environment-Safety (HES) effects associated with silica dust. In processes such as fracking, frac sand can produce breathable crystalline silica dust, which is a potential exposure hazard. Long term exposure to or breathing excessive amounts of crystalline silica can result in silicosis, which is a respiratory disease that causes scarring in lung tissue. Once silicosis has begun, medical treatment can be difficult. Therefore, proper handling of the frac sand to avoid overexposure to silica dust is important.

Silica exposure may occur in a number of jobs, including road work, drilling of oil or concrete, glassmaking, sandstone work, and some manufacturing processes. Despite the risk of silicosis, workers may not always have adequate safety equipment that could reduce their risk of illness from exposure to silica sand.

To protect, for example, oil field workers, drilling companies and other stakeholders associated with hydraulic fracking have adopted HES regulations to prevent overexposure to silica dust by workers or others who may be in the vicinity. Therefore, there is a need for systems and methods of monitoring the different levels of airborne crystalline silica dust (and other hazardous chemicals used in fracking) by on-site stationary and mobile sensors and off-site desktop and mobile application to protect against overexposure to silica dust.

DETAILED DESCRIPTION OF DISCLOSED EMBODIMENTS

The Figures described above and the written description of specific structures and functions below are not presented to limit the scope of what Applicants have invented or the scope of the appended claims. Rather, the Figures and written description are provided to teach any person ordinarily skilled in the art to make and use the embodiments for which patent protection is sought. Those skilled in the art will appreciate that not all features of a commercial embodiment are described or shown for the sake of clarity and understanding. Persons of skill in this art will also appreciate that the development of an actual commercial embodiment incorporating aspects of the present disclosure will require numerous implementation-specific decisions to achieve the developer's ultimate goal for the commercial embodiment. Such implementation-specific decisions may include, and likely are not limited to, compliance with system-related, business-related, government-related and other constraints, which may vary by specific implementation, location, and from time to time. While a developer's efforts might be complex and time-consuming in an absolute sense, such efforts would be, nevertheless, a routine undertaking for those of ordinary skill in this art having benefit of this disclosure. It must be understood that the embodiments disclosed and taught herein are susceptible to numerous and various modifications and alternative forms. Lastly, the use of a singular term, such as, but not limited to, "a," is not intended as limiting of the number of items. Also, the use of relational terms, such as, but not limited to, "top," "bottom," "left," "right," "upper," "lower," "down," "up," "side," and the like are used in the written description for clarity in specific reference to the Figures and are not intended to limit the scope of the disclosure or the appended claims. When referring generally to such elements, the number without the letter is used. Further, such designations do not limit the number of elements that can be used for that function. The terms "couple," "coupled," "coupling," "coupler," and like terms are used broadly herein and can include any method or device for securing, binding, bonding, fastening, attaching, joining, inserting therein, forming thereon or therein, communicating, or otherwise associating, for example, mechanically, magnetically, electrically, chemically, operably, directly or indirectly with intermediate elements, one or more pieces of members together and can further include without limitation integrally forming one functional member with another in a unity fashion. The coupling can occur in any direction, including rotationally. The terms "including" and "such as" are illustrative and not limitative. The term "can" as used herein means "can, but need not" unless otherwise indicated. Each structure, component and other item included herein will have certain inherent physical characteristics when and if present in one or more physical embodiments of the present embodiments, such as dimension(s) (e.g., height, width, length, diameter), mass, weight, imaginary axes, cross-sections and the like. It will be understood by a person of ordinary skill in the art that such characteristics are present, and that such items exist in one or more environments, regardless of whether expressly described or mentioned herein.

In one embodiment, a system for monitoring levels of airborne crystalline silica dust and/or other hazardous chemicals or materials used in fracking or other operations is provided. A monitoring system can include one or more onsite stationary or mobile sensors, one or more offsite stationary or mobile sensors, and one or more onsite or offsite desktop or mobile applications. By real time processing data acquired from on-site stationary and/or mobile sensors, the system of this embodiment can track and convey airborne particulate data, which can include providing visualization of an exposure map, such as of a fracking or other work site, through one or more electronic or software applications. The terms "sensor" and "sensors" are used broadly herein and can include sensor modules, assemblies or other systems each comprising a sensing device and one or more other components, such as components for transmitting, receiving, powering, coupling, communicating, or displaying, or for performing other functions, separately or in combination.

Figure 1:
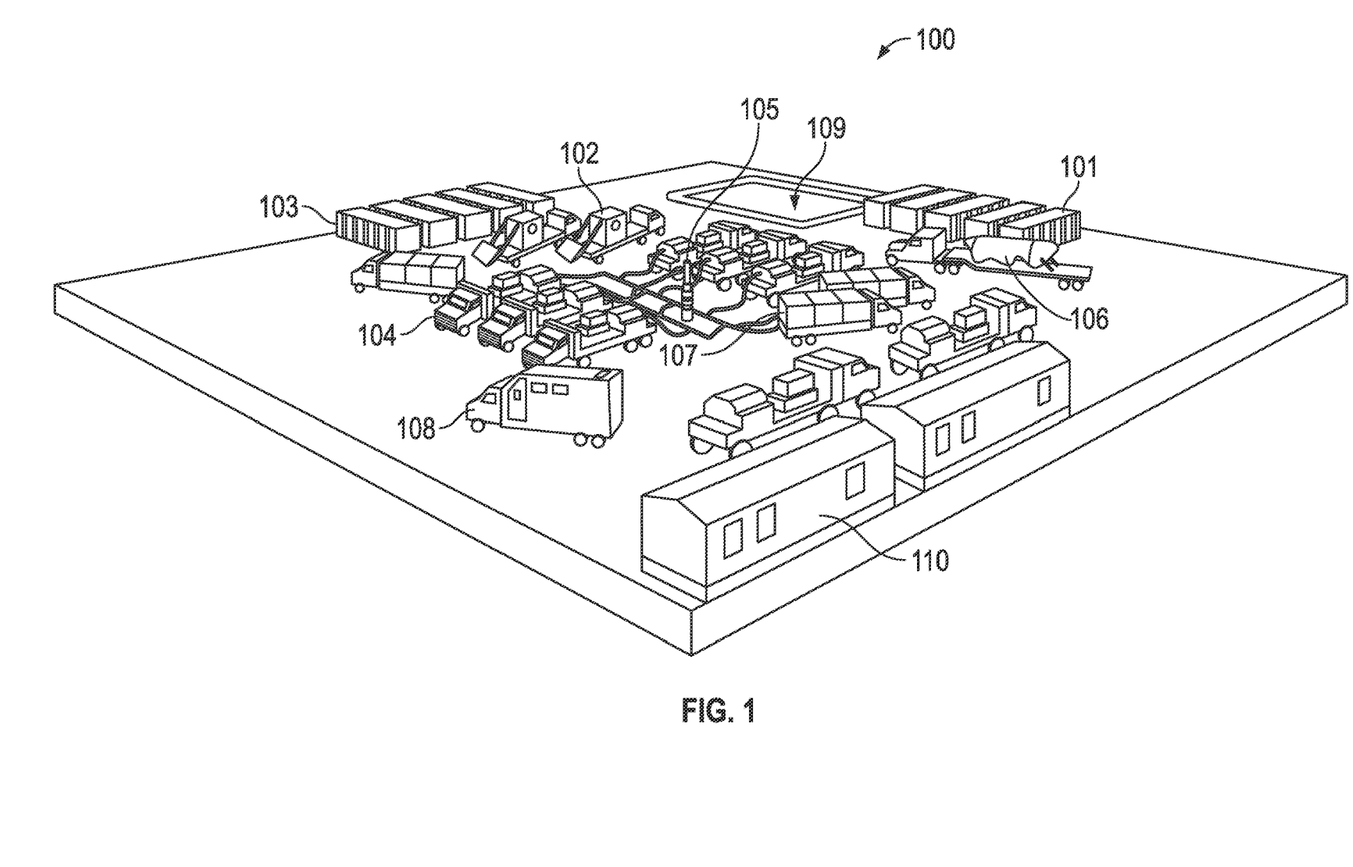
FIG. 1 is a schematic perspective view illustrating an exemplary hydraulic fracturing site for monitoring according to the disclosure.

FIG. 1 is a schematic perspective view illustrating an exemplary hydraulic fracturing site 100 for monitoring according to the disclosure. Sand used in hydraulic fracturing operations, or "frac sand," can be stored in one or more sand storage units 101 after being trucked or otherwise delivered to the site and frac fluid can be stored in one or more frac storage tanks 103. Sand can be blended or mixed with fluid and one or more chemicals in frac blenders 102, such as prior to pumping. Frac pumps 104, such as pumping trucks or other pump assemblies, can pump a frac mixture into a well bore through a wellhead 105. A fracturing site 100 or other work site can of course include other equipment and structures related to an application at hand, such as, for example, sand trucks 106, chemical storage trucks 107, data monitoring trucks 108, fluid sources 109, buildings 110, such as for office space or living quarters, or other items, separately or in combination, temporarily or otherwise. Although care can be and often is taken, there may be opportunities for frac sand to escape one or more of the foregoing system components into the surrounding environment or atmosphere, creating a need for a suitable system to monitor the silica levels in the environment, both on and off site, to which workers or other persons may be exposed due to escaped sand or other materials.

Figure 2:
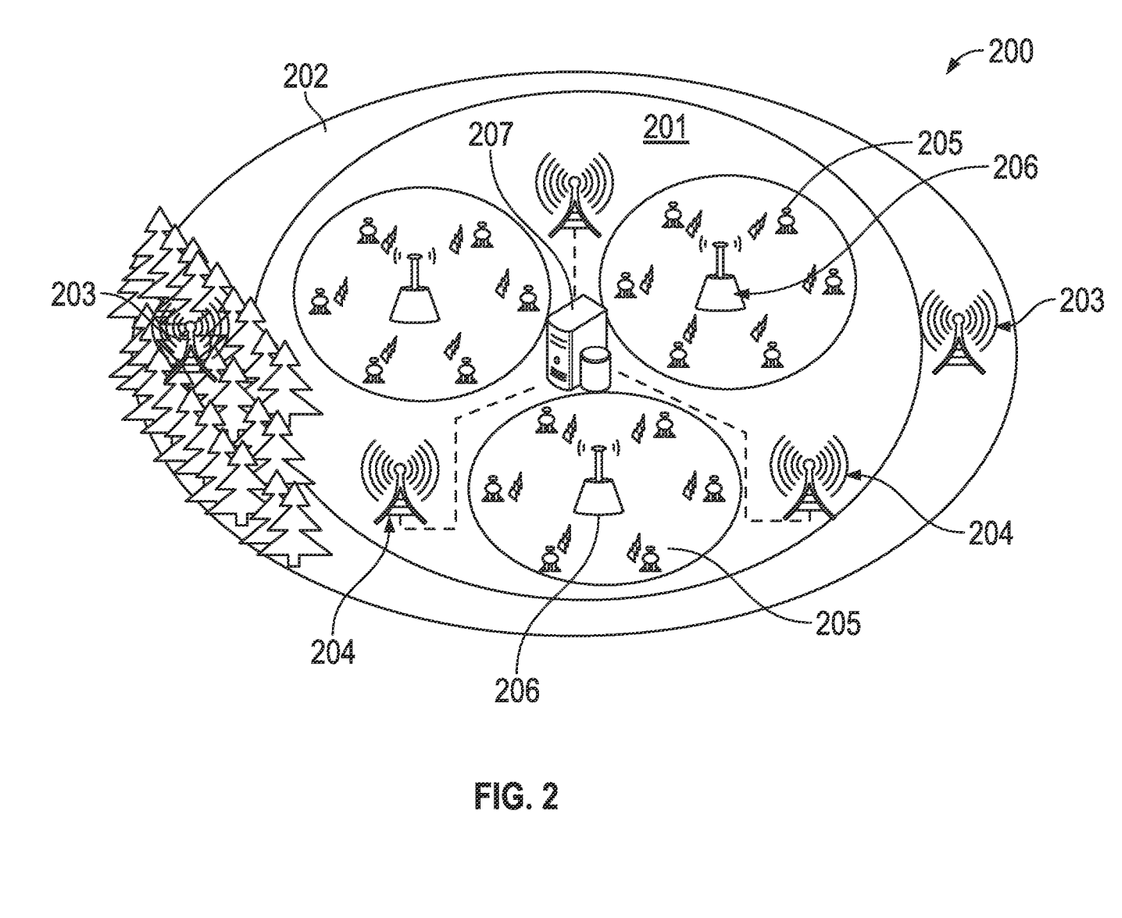
FIG. 2 is a schematic diagram illustrating one of many embodiments of a monitoring system according to the disclosure.

FIG. 2 is a schematic diagram illustrating one of many embodiments of a monitoring system 200 according to the disclosure. System 200 can be divided into two or more networks, such as an onsite sensory network 201 and an offsite sensory network 202, and can include one or more offsite sensors 203 and one or more onsite sensors 204. A plurality of onsite sensors 204, such as stationary or fixed (temporarily, permanently or otherwise) sensors, can be provided in an onsite sensory network for monitoring one or more silica concentrations in the ambient air (or elsewhere, e.g., in a building or structure) onsite. A plurality of offsite sensors 203 can be arranged to measure the silica levels in one or more areas offsite. Onsite sensors 204 can provide information reflecting the silica level(s) that someone working on the site would be exposed to during the course of his or her duties (e.g., over a period of time, which can be any period of time) and can provide information regarding the overall silica levels on the site itself. The offsite sensors 203 can measure silica levels off-site, which can provide a measure or baseline for silica levels in the air attributable to the environment itself (i.e., independent from any fracking or other man-made operations that may be present). Further, offsite sensors 203 can provide a method for detecting an increase in airborne silica concentration, and can be arranged or configured to alert site operators or other persons that silica dust from a site is migrating into a surrounding environment. This type of migration can be caused, for example, by an increase or shift in wind speed or direction.

System 200 can include one or more mobile sensors 205. A mobile sensor may be carried or worn by a worker or other person at a work site. Mobile sensors 205 can provide a direct measurement of the silica levels a corresponding worker may be exposed to. In at least one embodiment, a record of silica exposure levels can be maintained on a mobile sensor 205 itself and can be collected periodically, for example, by downloading or otherwise collecting data from the sensor. In one or more other embodiments, it can be advantageous, however, for a mobile sensor 205 to provide real-time data transmission to one or more other devices, such as to a central computing system that can record and/or aggregate the data measured by all sensors in the system, which can be any number of sensors required by a particular application, including stationary and mobile sensors, separately or in combination. Such transmission, in at least one embodiment, can be provided by a wireless connection to one or more base stations 206, which can wirelessly or otherwise transmit the data to a central computer 207. In one or more embodiments, the base station 206 can be or include one or more conventional cellular telephone towers. A wireless transmission may be performed by cellular transmissions, WiFi transmissions, or, as another example, by proprietary radio transmissions. Similarly, the stationary sensors can be coupled to a central computer 207 by wireless means, although, for the stationary sensors, one or more wired connections can also be used as a matter of design choice, separately or in combination with one or more wireless connections, in whole or in part. One or more stationary sensors can also communicate with a central computer 207 through conventional cellular transmissions, if desired or required for a particular applications. In at least one embodiment, one or more of sensors 203, 204 can transmit the silica level information to a base station 206, which can forward such data to a central computer system 207.

One suitable sensor (one of many) for use as a mobile sensor 205 is the M-Dust particle sensing unit available from my Hermes S.r.l. A suitable sensor (one of many) for use as a stationary sensor 203, 204 is the high volume sampler PM1025/UNE available from MCV, S.A. Other suitable sensors, whether presently existing or future developed, will be known to those of skill in the art having the benefits of the present disclosure, and can be adapted as a design choice. In at least one embodiment, which is but one of many, one or more of sensors 203, 204, 205 can be a sensor that measures airborne particulates in general, and an assumption can be made within the system regarding a correlation between airborne particulates and silica, such as that there is a linear or other correlation between silica dust and air borne particulates measured by a sensor. Alternatively, or collectively, another sensing device can be disposed at one or more representative points in the system and can perform a more thorough or micro analysis (e.g., chromatography or similar) on a periodic or other basis (e.g., every hour), which can depend on how long such a deeper analysis may take, such as in order to measure or at least approximate an actual percentage of silica dust present within a dust cloud or area. Such a determination, which can be a ratio, for example, can be considered constant across a field or other area for a period of time, such as until a subsequent data reading, sample or other update takes place.

Figure 3:
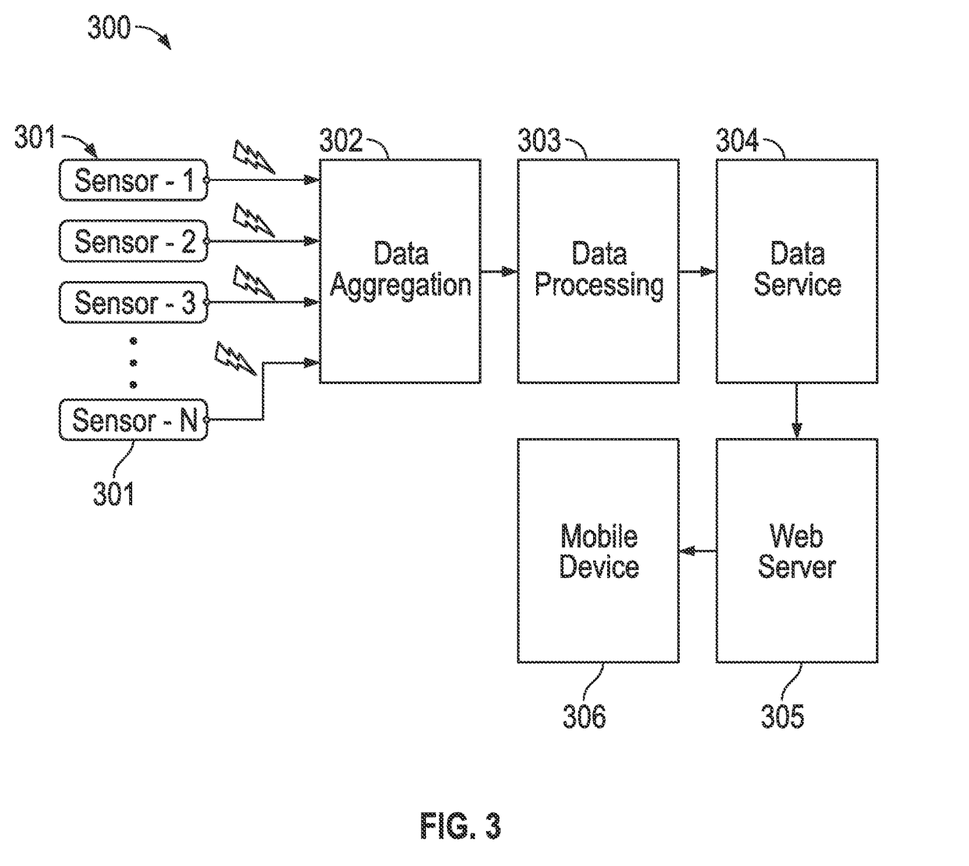
FIG. 3 is a block diagram illustrating one of many embodiments of a monitoring system according to the disclosure.

FIG. 3 is a block diagram illustrating one of many embodiments of a monitoring system according to the disclosure. System 300 can comprise one or more sensors 301 for sensing and wirelessly or otherwise transmitting information regarding silica levels in the atmosphere (or a corresponding portion thereof) to one or more other components of the system, such as a data aggregator 302. The system may also include one or more computer processors for data processing, data service, and/or web service, as further described below. It will be understood that a computer system according to one or more embodiments of the disclosure can be arranged from a plurality of separate computer processors, each of which performs one or more tasks, or all tasks can be performed by a single computer. The exact arrangement and selection of computer(s) is a matter of design choice within the capabilities of one skilled in the art, and the arrangements depicted and described herein are illustrative of particular, exemplary embodiments.

One or more sensors 301 can collect data from a work field and forward, transmit or otherwise provide collected data to a base station, such as a nearest base station, which can act as an aggregator. One or more sensors can be deployed in two different modes: stationary sensors, which can gather regional information about an amount of silica in an environment, and mobile sensors, which can be useful for measuring silica that an individual worker might be exposed to as he or she moves about the work site. Stationary sensors can be deployed either wired or wirelessly to collect data. Mobile sensors can be mounted with electronic sensor technologies to sense and record crystal silica exposure by specific workers directly. One or more sensors can transmit silica level information to a base station, separately or in combination with additional information, such as a time stamp reflecting when each measurement was taken, and/or a Global Positioning System ("GPS") coordinate reflecting the location of a sensor when one or more measurements were made. Of course, in one or more other embodiments, it may not be necessary to transmit the GPS coordinate(s), e.g., for one or more stationary sensors with known locations. Offsite sensors can measure a silica level of exposure at distant locations (which can be any distance from a site), which can allow an operator to take action, if necessary or desirable, to protect the environment or a portion thereof, such as proactively or otherwise. Any crystalline silica material received in a sensor can be sensed and quantitatively measured and/or reported, separately or in combination, in whole or in part.

In at least one embodiment, a mobile sensor sampling rate can be varied or at least variable depending on the circumstances of an application at hand. For example, when a worker is close to a hydraulic fracturing area or another location where exposure to airborne particles can be expected to occur, a sampling rate of one or more sensors can, but need not, be increased. As another example, when a worker is a distance away from a hydraulic fracturing area or other location where exposure to airborne particles can be expected to occur, which can be any distance, a sampling rate of one or more sensors can, but need not, be decreased. As a further example, a sampling rate of one or more sensors can, but need not, be further decreased when a worker is an additional distance away from such an area, which can be any distance. A sampling rate can be increased or decreased in any manner and magnitude according to an application, and such changes can occur at any time. For example, a sampling rate can change from a first rate to a second rate immediately upon a mobile sensor being moved from a first distance to a second distance from a location, or a sampling rate can change gradually as a sensor moves over a distance. In at least one embodiment, which is but one of many, a fracking or other work location can include or be defined to include one or more areas or zones, such as a safe zone, an unhealthy zone, a hazardous zone, or one or more other zones, such as zones between or outside of the foregoing zones, separately or in combination. If a worker or other person having one or more sensors resides in a hazardous zone, a sampling frequency can be increased relative to a sampling frequency on one or more other zones, such as by being increased by 2, 3, 4, 5, 6, 7, 8 . . . n times higher than when he or she is located in a safe or other less hazardous zone, and vice versa. In at least one embodiment, a monitoring system can be or include a dynamic sampling system and the sampling of the measured silica level can be adaptive. One or more sensors can measure a silica or particulate level constantly or, as another example, periodically, such as every minute, every 2, 3, 4, 5, 6, 7, 8 . . . n minutes, etc., depending on the system settings for an implementation at hand. One or more locations of hydraulic fracking or other work operations or portions thereof can be fixed, and can be known by the system, such as by way of being programmed into or otherwise defined within one or more system components (e.g., a memory component). Each monitored individual can have at least one mobile sensor, which can include, for example, a silica sensor, a GPS sensor and a processing unit, separately or in combination with one or more other system components, such as a power source, transmitter or receiver. The distance of a user relative to a fracking or other work location can be calculated in the user's mobile sensor. As the user moves closer to and further from a fracking location or other danger zone, a sensor's measurement rate of particulates can be respectively increased and decreased accordingly. Each of the one or more zones can be at least partially defined by data collected from one or more stationary sensors, and the zone areas or definitions can, but need not, change over time, such as depending upon an amount of airborne particulates that may be present. As one or more zones change, measurement rate of one or more mobile sensors can, but need not, also change, such as in response to recognition of a newly defined or redefined zone. A sampling rate of one or more sensors can also change or be adjusted based on one or more factors other than positioning relative to one or more locations, such as, for example, based upon reaching a chosen level of particulate exposure, elapsed time, wind direction, temperature or other environmental conditions, separately or in combination. One or more mobile sensors can, but need not, alert a user or other person to one or more states or conditions, such as upon reaching a level of particulate exposure, moving from one zone to another, sensing an increase or decrease in particulates present, low battery or other occurrences, separately or in combination. For example, a sensor can include a display or other interface for allowing a user to observe or read relevant information. As other example, a sensor can include an alert system, which can include an alarm system (e.g., sound, vibration), a messaging system, such as for sending text messages, emails, phone calls, or other data or signals, or other systems, such as a data transmission system, separately or in combination.

Fixed sensors, such as the PM 2.5 High Volume Sensor, can be advantageously placed at approximately the same height at which an average person would most often be breathing, for example, between 4 and 6 feet from ground level. Of course, this need not be the case, and in one or more other embodiments fixed sensors can be placed at one or more different heights, for example, heights or other locations at which workers or other persons may be sitting or standing during work operations, such as one or more locations above or below ground level. Mobile sensors, such as the M-Dust Particle sensor, can be worn or otherwise carried by workers and other users in any manner for measuring silica exposure associated with an individual, such as, for example, by helmet mount, belt mount, clip mount or other holding configurations, such as by being coupled to one's clothing or body, or being worn around one's neck.

With continuing reference to FIG. 3, in at least one embodiment, one or more sensors 301 can include bluetooth, infrared or other wireless communication components, such as for transmitting silica concentration and other data to a cellular telephone, computer or other device, which can forward or otherwise communicate such information to one or more corresponding data aggregators 302 (hereinafter "data aggregator 302"), such as one or more data aggregation computers. Data aggregator 302 can perform one or more functions for integrating information provided by one or more sensors 301 in a useful manner. For example, a data aggregator 302, in at least one embodiment, can average silica level measurements taken by a group of sensors based on their location or, in another embodiment, can average measurements or other values collected by a sensor or group of sensors over a period of time. In this way, in at least one embodiment, an amount of data can be reduced and provided to a site operator or other receiver in a manner that can be interpreted by or otherwise useful to the receiver, whether as received or as proceed after being received, in whole or in part. Data aggregation can be performed in different ways, which can include any manner of data aggregation in accordance with an application or an embodiment. For example, a set of values or other measurements measured over a period of time (time window) can be averaged to one or more values or sets of values and this information can be transmitted to one or more other components of a monitoring system. As another example, measured data over a period of time can be compared to a chosen value, such as a threshold value, and if one or more values are greater than a threshold value then such value(s) can be transmitted. Similar methodology can be employed based on a location of a sensor or other factors, separately or in combination with one another or a time window as described above.

A data aggregator 302 can provide data to one or more data processors 303 (hereinafter "data processor 303"), such as a data processing computer, for processing data, such as by performing one or more calculations based on some or all of the data received. Data processor 303 can include any hardware required by a particular application, such as one or more processors, memories, power sources, monitors, and other components, such as servers and communication equipment, separately or in combination, whether now known or future developed. Data processor 303 can include software for processing the data, such as by performing one or more calculations based on some or all of the data received, which can, but need not, include downloadable and non-downloadable software or services accessible via a network, such as the Internet or an intranet network. In at least one embodiment, which is but one of many, a monitoring system can include one or more relational database management systems, which can, but need not, include a cloud-ready information platform, such as SQL Server available from Microsoft (which is but one of example of many) or another platform that can be integrated with system infrastructure. In at least one embodiment, one or more data processors 303 can record measurements from one or more sensors, such as fixed and/or mobile sensors, and can store such data in a database. A data processor 303 can generate one or more reports based on provided data, such as an interactive or other report for conveying one or more values or other results to a user.

Data from one or more sensors, such as mobile sensors, can be useful to track each individual worker's exposure to silica dust or other particulates. This information can be cross-referenced with guidelines, such as standards set or otherwise put in place by, for example, an industry regulation authority, a medial or environmental authority, a governmental authority (e.g., the Occupational Safety and Health Administration ("OSHA"), or another public or private entity or committee, such as an employer or operator, to at least help ensure that no worker is over-exposed to silica dust or other potentially harmful materials. In at least one embodiment, measured exposure information can be used in conjunction with regional measurements of an environment's natural silica levels so that a worker's exposure to frac dust, if any, can be distinguished from his or her exposure to silica naturally present in the environment itself. For example, a regulation or other authority may determine or otherwise set a standard for a maximum amount of silica dust or other material that an individual can be exposed to over a period of time. At least one embodiment of a monitoring system according to the disclosure can use one or more of such standards as references and can alert (e.g., in one or more of the manners described above) workers or other individuals if a person's exposure nears, reaches and/or exceeds such standards. For example, a system can track or otherwise monitor an exposure trend, such as for determining whether an exposure trend can or will lead to a potential over-exposure, such as over an amount of time according to an individual's work schedule. For instance, a monitoring system can run or otherwise perform a trend calculation and can determine how much time remains before an individual will reach or exceed a maximum allowable exposure, such as a periodic exposure (e.g., daily, weekly, monthly, annually, etc.) based on one or more levels of exposure during such a period (which can include variable or varying levels of exposure). In at least one embodiment, a standard or regulation can include a definition of or otherwise call for adequate Personal Protective Equipment (PPE) according to ambient silica levels, and a monitoring system can alert a user that exposure levels are increasing and that usage of additional protection (e.g. dust masks, goggles, respirators, hazardous materials ("hazmat") suits, etc.) may be required or recommended at one or more times or while located in one or more areas of zones.

In at least one embodiment, a data processor 303 can execute or otherwise perform one or more algorithms including collected data for providing spatial, temporal, or other information relating to silica levels on or around a site. For example, collected silica level data can be interpolated to determine silica levels at one or more unmeasured or unmonitored locations on a site, such as locations corresponding to one or more GPS or other coordinates, for example. This can allow a system to monitor spatial-temporal exposures through a drilling field and other areas or locations. In one or more embodiments, an interpolation can be a linear interpolation, such as based on a distance of each unmeasured/unmonitored location relative to one or more sensors. For example, a system can include a Graphical Information System (GIS) employing one or more interpolation techniques, such as the so-called Voronoi approach. Within an embodiment of a system according to the disclosure, a fracking or other worksite can be modeled as a grid composed of cells covering some or all of the site. Silica levels can be measured at one or more cells (e.g., locations of stationary sensors) in the grid, and these measurements can be extrapolated or interpolated to estimate silica levels at other cells in the grid. Computing silica levels at unmeasured GPS coordinates or other locations can allow an operator to quantify an amount of airborne silica or other particles in the atmosphere and tally or otherwise record them for future reference, such as in order to determine or estimate quantities to which non-workers, for example, individuals off-site, might be or have been exposed, or to distinguish an amount of naturally occurring or "background" silica or other matter.

One or more data servers 304 can provide a communication channel between data processor 303 and one or more web servers 305. Data server 304 can handle various system tasks, including data storage, data analysis, data manipulation, archiving and security, separately or in combination, in whole or in part. For example, in at least one embodiment, data processing in data processor 303 can be processing of gathered data to store in a database, and data server 304 can hold processed data as well as responses from a web server 305. Data generated by or from one or more mobile devices 306 can also be stored on a data server 304, which can include using a web server 305 as an intermediary. In one or more embodiments, the architecture of data server 304 can be accessed on the client side and the server side, such as to provide a link between front and back ends of the system or one or more system components. A system can include architecture for providing increased functionality of a data base management system ("DBMS"), such as a DBMS that synchronizes a client and a server. For example, once synchronized, newly gathered or other data can be available to one or more servers and can be provided to one or more front-end clients, such as a mobile device 306 or other client (e.g., a website). This can be beneficial, for example, because data can be synchronized across various platforms without changing the data source or using a different web server. In other words, web server 305 can network from client to client using client/server architecture data accessibility, and can provide consistent data to different clients (e.g., websites, phones or other mobile devices, computers, etc.), for example, so that one user's account appears at least partially the same across multiple platforms. Server 305 can provide communication between system components over a network, such as by way of the Internet or World Wide Web. In at least one embodiment, server 305 can provide communication between the DBMS and one or more clients for accessing information about silica levels measured by sensors 301. Web server 305 can, but need not, employ cloud-based computing technologies, which can include providing or accessing reliable, scalable, at least substantially instant, or other services over the Internet or another network for one or more users (e.g., a commercially available cloud service). In this manner, one or more embodiments can synchronize data such as photos, login credentials, emails, etc. across various devices using cloud-based technologies. Server 305 can host one or more websites for allowing authorized or other users to access data or information based on data from one or more sensors 301. In such an embodiment, which is but one of many, server 305 can send queries to access silica level data in one or more data servers 304, such as using Hypertext Transfer Protocol ("HTTP"). This can allow a web server 305 to function as a part of a system for monitoring, serializing and de-serializing one or more data objects. In at least one embodiment, one or more mobile sensors 301 can communicate with one or more mobile devices 306, such as a smartphone or other cellular device, worn or carried by a worker. A mobile device 306 can be equipped with Wi-Fi, Bluetooth or other systems that can allow or provide connections to the Internet (or another network), and a GPS to provide worker location information (e.g., when outdoors). Such portable devices can make information and services available virtually anywhere and at any time in the drilling field or other work environment. A mobile device 306 can allow individual workers to know a level of exposure to silica or other materials at any time required by a particular application, as well as a dynamic rate of change on a continuous basis for an extended spatial area.

Figure 4:
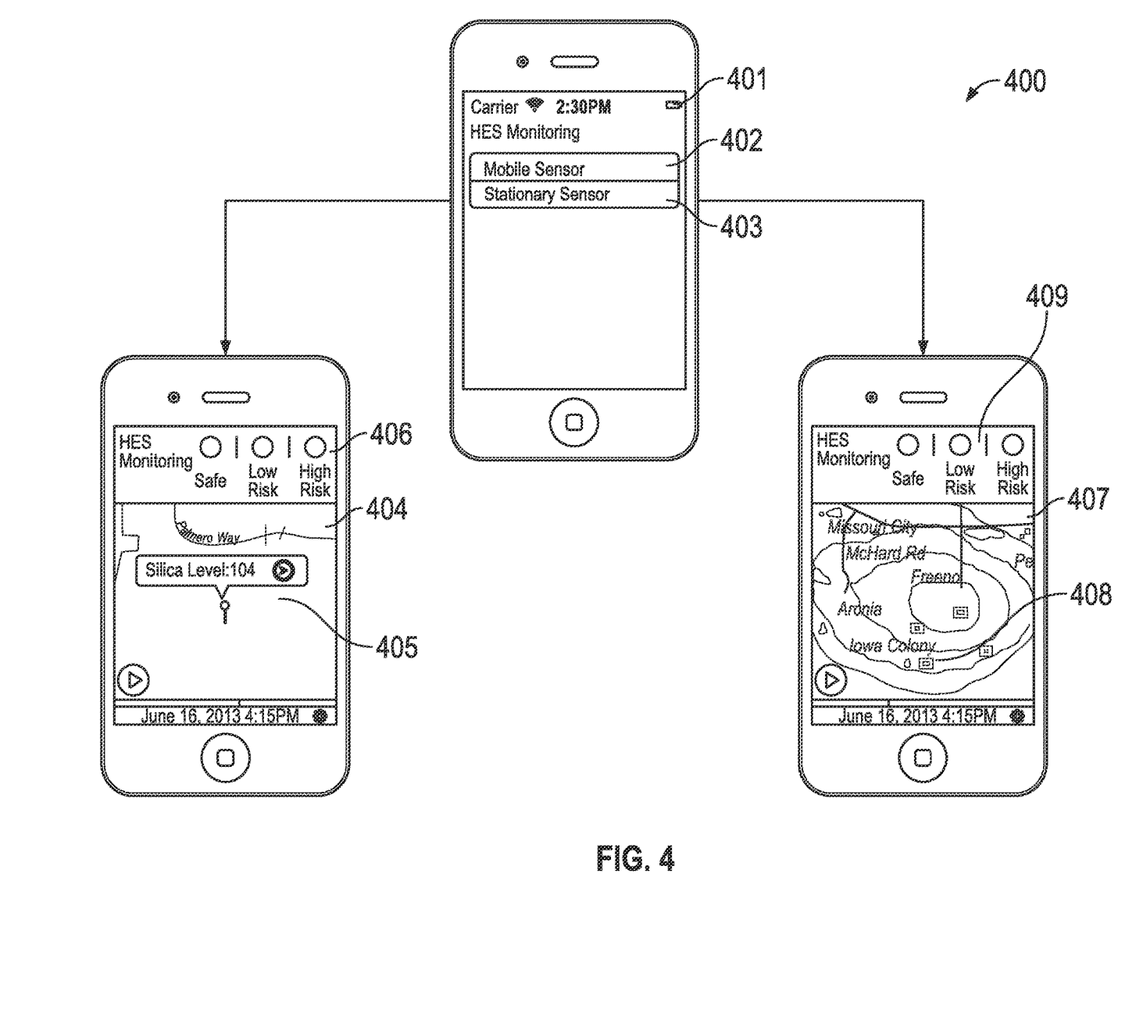
FIG. 4 is a front view of one of many embodiments of a monitoring system mobile device according to the disclosure.

FIG. 4 is a front view of one of many embodiments of a monitoring system mobile device 400 according to the disclosure. FIG. 4 illustrates an embodiment in which silica level information can be conveyed through at least one dynamic visual display on one or more mobile devices 400, and depicts three views of an exemplary mobile communication device to illustrate optional aspects of an embodiment. The illustrative embodiment shown is implemented as a mobile application (or "app") running on a mobile telephone, but this is of course only one of many examples of an embodiment. Mobile device screen 401 can present a user with one or more selection boxes 402, 403, for allowing the user to select for viewing silica levels from one or more sensors, such as mobile sensors and stationary sensors. Touching or otherwise selecting a mobile sensor selection box 402 can cause the app to present mobile device screen 404, which can display a map of an area (e.g., where the user is located) overlaid with a pinpoint icon 405 identifying a location of the user or mobile device. Pinpoint icon 405 can display at least substantially real-time or other silica level readings as measured by a mobile sensor or sensors carried by the user, which can transmit silica level readings through, for example, a Bluetooth or other connection (which can be wired or wireless) to one or more mobile devices 400. This can allow the user to know his or her potential exposure and can prompt the user to take measures, such as using respiratory protection equipment or performing adjustments to operating equipment, to manage exposure if needed or desired. In at least one embodiment, a system can include one or more indicators 406, such as bars, icons or other symbols, for providing a user with input or other data pertaining to his or her current exposure level. For example, one or more indicators 406 can be color coded, shape coded, size coded, audio coded, or otherwise designed or displayed to indicate a range of exposure levels and where a user's existing exposure level fits within the range (which can include any range according to an implementation or worksite). Screen 404 can provide an at least substantially instantaneous or other readout of the silica levels that can be used by the worker carrying the device or any other worker reading the device. Screen 404 can also display other relevant information, such as the cumulative or total exposure levels received by a user over a time period, such as a workday or shift, and a rate of change in exposure levels. In one or more embodiments, a screen can provide a display of a predicted exposure over a period of time based on current or other conditions, such as estimated conditions. For example, a static sensor or other map can be overlaid with a wind map to predict movement of silica or other particulates over time. A prediction can be made, such as at a central computer system, and such information can be forwarded to one or more mobile communication devices for display to or other use by an app and/or user. For example, levels of exposure to respirable silica dust can be reduced or significantly lower when wind velocity in an area is sensible compared to exposure levels in the area when wind velocity is not sensible. A system can factor these and other considerations into one or more calculations and can alert workers in a path of the silica dust, such as to prompt appropriate protective measures.

Returning now to mobile device screen 401, touching on or otherwise selecting a stationary sensor box 403 can present a user with an interface, such as a dynamic visual display, based on information from one or more fixed sensors, which can include the delivery of additional detailed spatial-temporal information in real or other time. In at least one embodiment, such as depicted in mobile device screen 407 for illustrative purposes, silica levels can be displayed in a contour map, such as a map overlaid on a map of a worksite or other area. A contour map can be assigned one or more colors for different levels of silica measurements, with, for example, darker colors or shades representing relatively higher levels of silica dust in the atmosphere and lighter colors or shades representing relatively lower levels of silica dust in the atmosphere (or vice versa). Also overlaid on screen 407 can be one or more icons 408 representing the locations of sensors and/or other landmarks that may be desired by or informative to a user. A contour map can give workers an overview of silica levels in a mapped area and can track movement of silica dust across an area, such as based on wind changes or other environmental conditions. A display, such as screen 407 or another interface, can include one or more indicators 409 (e.g., similar to indicators 406) for providing a user with a real time or other indication of his or her silica levels at one or more specific locations. For example, like a radar or similar style of data representation, one or more polygons of other shapes can represent different levels of silica exposure, which can provide a user with a quick or otherwise user-friendly visualization of exposure levels or other magnitudes or amounts.

In at least one embodiment, mobile device 400 can be or include goggles or other eyewear, and a real-time silica exposure display can be implemented directly into the eyewear (e.g., Google Glass or other eyewear having a user interface). In such an embodiment, a shadow can be overlaid on top of a plain view (i.e., an augmented reality view) and the shadow can change (e.g., become darker) as a level of particle exposure increases and decreases. At a predetermined silica level in accordance with an implementation, the shadow overlay can become fully obscure (e.g., black), which can indicate that a user should take measures to at least reduce exposure. In at least one embodiment, one or more mobile devices 400 can be provided with an "offline" (or off-network) mode and can record cumulative or other exposure information if, for example, the mobile device cannot be fully turned on or cannot communicate with other parts of the system (e.g., when a user may be in a location outside of cellular or other network coverage). Each sensor, mobile device, or combination thereof can include a telecommunication protocol, which can be compliant with any applicable class rules (e.g., rules or regulations pertaining to wireless/wired communication devices, such as for establishing communication in simplex or duplex mode).

In at least one embodiment, there can be provided a real-time silica monitoring system comprising one or more stationary sensors positioned at geographic locations off-site from a hydraulic fracturing well site that detect and measure quantities of airborne silica particles, one or more on-site stationary sensors positioned at geographic locations on a hydraulic fracturing well site that detect and measure quantities of air-borne silica particles, one or more mobile sensors suitable to be carried by individual persons on-site that detect and measure quantities of airborne silica particles, and a computer system that aggregates and stores the airborne silica measurements taken by the off-site stationary sensors, the on-site stationary sensors, and the mobile sensors. A real-time silica monitoring system can include at least one mobile communication device suitable to be carried by an individual person on-site and that can receive data from at least one of a plurality of mobile sensors, such as data representing a quantity of airborne silica particles measured, and that can transmit the data to a computer system. A mobile communication device can receive data from a computer system, such as data representing at least one of an on-site and an off-site airborne silica level and can provide a visual display of the received data. A mobile communication device can display received data representing on-site and off-site airborne silica levels on a map, such as a contour map, and can receive data from one or more mobile sensors over a wireless communication protocol, such as a Bluetooth wireless communication protocol. One or more mobile communication devices can communicate with a computer system through an Internet communication protocol.

In at least one embodiment, there can be provided a method for real-time silica monitoring comprising providing a plurality of off-site sensors positioned at geographic locations off-site from a hydraulic fracturing well site that detect and measure the quantity of airborne silica particles, providing a plurality of on-site sensors positioned at geographic locations on a hydraulic fracturing well site that detect and measure the quantity of air-borne silica particles, providing a plurality of mobile sensors suitable to be carried by individual persons on-site that detect and measure the quantity of airborne silica particles, and aggregating and storing the airborne silica measurements taken by one or more of the off-site sensors, the on-site sensors, and the mobile sensors. A method for real-time silica monitoring can include providing at least one mobile communication device suitable to be carried by an individual person on-site or elsewhere, receiving on a mobile communication device data from at least one mobile sensor representing a quantity of airborne silica particles measured by the sensor, and transmitting the data to a computer system. A method can include receiving on a mobile communication device data from a computer system representing at least one of an on-site and an off-site airborne silica level and providing a visual display of received data on the mobile communication device, which can include displaying the received data representing the on-site and off-site airborne silica levels on a contour map. A method can include receiving on a mobile communication device data from at least one mobile sensor over a wireless communication protocol, such as a Bluetooth wireless communication protocol, and can include communicating between the at least one mobile communication device and a computer system through an Internet communication protocol.

In at least one embodiment, there can be provided a computer readable medium having instructions stored thereon that, when executed by a processor, cause the processor to perform a method that can include receiving from at least one off-site stationary sensor positioned at a geographic location off-site from a hydraulic fracturing well site a measured quantity of airborne silica particles, receiving from at least one on-site stationary sensor positioned at a geographic location on the hydraulic fracturing well site a measured quantity of airborne silica particles, receiving from at least one mobile sensor suitable to be carried by an individual person on-site a measured quantity of airborne silica particles, aggregating the measured quantities of airborne silica particles received from at least one of the at least one off-site stationary sensor, the at least one on-site stationary sensor, and the at least one mobile sensor, and storing the measured quantities of airborne silica particles received from at least one of the at least one off-site stationary sensor, the at least one on-site stationary sensor, and the at least one mobile sensor. Receiving a measured quantity of airborne silica particles from one or more of at least one off-site stationary sensor, at least one on-site stationary sensor, and at least one mobile sensor can include receiving measured quantities of airborne silica particles from a plurality of sensors. A computer readable medium can include instructions stored thereon that, when executed by a processor, cause the processor to perform a method that can include receiving a quantity of airborne silica particles measured by one or more mobile sensors from at least one mobile communication device, and transmitting data representing at least one of an on-site and off-site airborne silica level to at least one mobile communication device. A computer readable medium can include instructions stored thereon that, when executed by a processor, cause the processor to perform a method that can include communicating with at least one mobile communication device through an Internet communication protocol, and transmitting data representing an airborne silica exposure level of one or more users to at least one device, such as a mobile communication device or other device.

While the disclosed embodiments have been described with reference to one or more particular implementations, those skilled in the art will recognize that many changes may be made thereto without departing from the spirit and scope of the disclosure. Further, the various methods and embodiments of the monitoring systems and methods can be included in combination with each other to produce variations of the disclosed methods and embodiments. Discussion of singular elements can include plural elements and vice-versa. References to at least one item followed by a reference to the item may include one or more items. Also, various aspects of the embodiments can be used in conjunction with each other to accomplish the understood goals of the disclosure. Unless the context requires otherwise, the word "comprise" or variations such as "comprises" or "comprising," should be understood to imply the inclusion of at least the stated element or step or group of elements or steps or equivalents thereof, and not the exclusion of a greater numerical quantity or any other element or step or group of elements or steps or equivalents thereof. The devices and systems may be used in a number of directions and orientations. The order of steps can occur in a variety of sequences unless otherwise specifically limited. The various steps described herein can be combined with other steps, interlineated with the stated steps, and/or split into multiple steps. Similarly, elements have been described functionally and can be embodied as separate components or can be combined into components having multiple functions. The embodiments have been described in the context of preferred and other embodiments and not every embodiment has been described. Obvious modifications and alterations to the described embodiments are available to those of ordinary skill in the art. The disclosed and undisclosed embodiments are not intended to limit or restrict the scope or applicability of the subject matter conceived of by Applicants, but rather, in conformity with the patent laws, Applicants intend to fully protect all such modifications and improvements that come within the scope or range of equivalents of the following claims.

What is claimed is:

1. A real-time silica monitoring system, comprising:
   a plurality of off-site stationary sensors positioned at geographic locations off-site from a hydraulic fracturing well site that detect and measure a quantity of airborne silica particles at their respective locations;
   a plurality of on-site stationary sensors positioned at geographic locations on the hydraulic fracturing well site that detect and measure a quantity of air-borne silica particles at their respective locations;
   a plurality of mobile sensors suitable to be carried by individual persons on-site that detect and measure a quantity of airborne silica particles;
   a computer system that aggregates and stores the quantities of airborne silica particles measured by the off-site stationary sensors, the on-site stationary sensors, and the mobile sensors; and
   at least one mobile communication device suitable to be carried by an individual user on-site that receives data representing the quantity of airborne silica particles measured from at least one of the plurality of mobile sensors and transmits the data to the computer system, wherein the mobile communication device receives data from the computer system representing at least one of an on-site and off-site airborne silica level and, based on the received data from at least one of the plurality of mobile sensors or from the computer system, provides a visual indicator representing the individual user's current silica exposure level with respect to a predefined range of exposure levels, and wherein the at least one of the plurality of mobile sensors is suitable to measure the quantity of airborne silica particles at a sampling rate that varies based on a distance the at least one of the plurality of mobile sensors is from the hydraulic fracturing well site, such that the sampling rate decreases the farther the mobile sensor is from the hydraulic fracturing well site.

2. The real-time silica monitoring system according to claim 1, wherein the mobile communication device displays the received data representing the on-site or off-site airborne silica levels on a contour map.

3. The real-time silica monitoring system according to claim 1, wherein the mobile communication device receives data from at least one of the plurality of mobile sensors over a wireless communication protocol.

4. The real-time silica monitoring system according to claim 1, wherein the mobile communication device communicates with the computer system through an Internet communication protocol.

5. A method for real-time silica monitoring, comprising:
   providing a plurality of off-site stationary sensors positioned at geographic locations off-site from a hydraulic fracturing well site that detect and measure a quantity of airborne silica particles at their respective locations;
   providing a plurality of on-site stationary sensors positioned at geographic locations on the hydraulic fracturing well site that detect and measure a quantity of air-borne silica particles at their respective locations;
   providing a plurality of mobile sensors suitable to be carried by individual persons on-site that detect and measure a quantity of airborne silica particles;
   aggregating and storing the quantities of airborne silica particles measured by the off-site stationary sensors, the on-site stationary sensors, and the mobile sensors;
   providing at least one mobile communication device suitable to be carried by an individual person on-site, receiving on the mobile communication device data from at least one of the plurality of mobile sensors representing the quantity of airborne silica particles measured, and transmitting the data to a computer system, wherein the at least one of the plurality of mobile sensors measures the quantity of airborne silica particles at a sampling rate that varies based on a distance the at least one of the plurality of mobile sensors is from the hydraulic fracturing well site, such that the sampling rate decreases the farther the mobile sensor is from the hydraulic fracturing well site;

receiving on the mobile communication device data from the computer system representing at least one of an on-site and off-site airborne silica level; and providing a visual indicator representing the individual user's current silica exposure level with respect to a predefined range of exposure levels.

6. The real-time silica monitoring method according to claim 5, further comprising displaying the received data representing the on-site or off-site airborne silica levels on a contour map.

7. The real-time silica monitoring method according to claim 5, further comprising receiving on the mobile communication device data from at least one of the plurality of mobile sensors over a wireless communication protocol.

8. The real-time silica monitoring method according to claim 5, further comprising communicating between the at least one mobile communication device and the computer system through an Internet communication protocol.

9. A non-transitory computer readable medium having instructions stored thereon that, when executed by a processor, cause the processor to perform a method comprising:

receiving from at least one off-site stationary sensor positioned at a geographic location off-site from a hydraulic fracturing well site a measured quantity of airborne silica particles;

receiving from at least one on-site stationary sensor positioned at a geographic location on the hydraulic fracturing well site a measured quantity of airborne silica particles;

receiving from at least one mobile sensor suitable to be carried by an individual person on-site a measured quantity of airborne silica particles;

aggregating the measured quantities of airborne silica particles received from the at least one off-site stationary sensor, the at least one on-site stationary sensor, and the at least one mobile sensor;

storing the measured quantities of airborne silica particles received from the at least one off-site stationary sensor, the at least one on-site stationary sensor, and the at least one mobile sensor;

receiving a quantity of airborne silica particles measured by a mobile sensor from at least one mobile communication device, the received quantity of airborne silica particles being measured by at least one of the plurality of mobile sensors that measures the quantity of airborne silica particles at a sampling rate that varies based on a distance the mobile sensor is from the hydraulic fracturing well site, such that the sampling rate decreases the farther the mobile sensor is from the hydraulic fracturing well site;

transmitting data representing at least one of an on-site and off-site airborne silica level to the at least one mobile communication device; and providing a visual indicator on the mobile communication device, the visual indicator representing the individual user's current silica exposure level with respect to a predefined range of exposure levels.

10. The computer readable medium of claim 9, wherein receiving a measured quantity of airborne silica particles from one or more of the at least one off-site stationary sensor, the at least one on-site stationary sensor, and the at least one mobile sensor further comprises receiving measured quantities of airborne silica particles from a plurality of sensors.

11. The computer readable medium of claim 9, further comprising instructions stored thereon that, when executed by a processor, cause the processor to perform a method comprising communicating with the at least one mobile communication device through an Internet communication protocol.

12. The computer readable medium of claim 9, further comprising instructions stored thereon that, when executed by a processor, cause the processor to perform a method comprising transmitting data representing an airborne silica exposure level of one or more users to the at least one mobile communication device.

* * * * *